United States Patent [19]

Esemplare

[11] Patent Number: 5,069,965

[45] Date of Patent: Dec. 3, 1991

[54] ARTICLES HAVING IMPROVED SLIP COATINGS

[75] Inventor: Pascal E. Esemplare, Mountainside, N.J.

[73] Assignee: Bioresearch, Inc., Farmingdale, N.Y.

[21] Appl. No.: 497,699

[22] Filed: Mar. 23, 1990

Related U.S. Application Data

[63] Continuation-in-part of Ser. No. 423,347, Oct. 18, 1989, abandoned.

[51] Int. Cl.$^5$ ............................................. B32B 25/08
[52] U.S. Cl. .................................. 428/330; 428/447; 428/516; 428/518; 428/520; 428/493; 428/494; 428/517; 427/412.3; 427/412.4; 427/302; 427/316; 524/504; 2/168; 264/300; 264/306
[58] Field of Search ............... 428/516, 517, 447, 330, 428/518, 520, 495, 494

[56] References Cited

U.S. PATENT DOCUMENTS

| | | | |
|---|---|---|---|
| 3,547,754 | 12/1970 | Tokos et al. | 428/516 |
| 4,436,788 | 3/1984 | Cooper | 428/483 |
| 4,956,232 | 9/1990 | Balloni et al. | 428/516 |

*Primary Examiner*—P. C. Sluby
*Attorney, Agent, or Firm*—Larson and Taylor

[57] ABSTRACT

Rubber and vinyl articles such as gloves with improved slip coatings and processes for their production are provided by coating the outer and/or inner surfaces with either (1) a copolymer of at least one copolymerizable vinyl halide, at least one copolymerizable ethylenically unsaturated hydrocarbon and at least one copolymerizable ethylenically unsaturated monomer containing a carboxyl or amido group, (ii) copolymer of at least one copolymerizable vinyl or vinylidene halide, acrylonitrile and at least one acrylic monomer, or mixtures of (i) and (ii).

27 Claims, No Drawings

ARTICLES HAVING IMPROVED SLIP COATINGS

BACKGROUND OF THE INVENTION

This application is a continuation-in-part of application Ser. No. 07/423,347 filed Oct. 18, 1989, now abandoned.

BACKGROUND OF THE INVENTION

This invention relates to rubber and vinyl articles having improved slip coatings and to compositions and methods of providing same. More particularly, the invention relates to rubber and vinyl articles, such as sterile surgeons' gloves, which are provided with an improved slip coating.

It has previously been proposed to provide slip finishes on rubber and vinyl articles such as rubber gloves or girdles by various methods. For example, the surface of a rubber glove can be halogenated with bromine or chlorine to make it slippery. However, this treatment may result in very poor aging properties. Discoloration can begin almost immediately and, within a month, the halogenated surface may become hard and brittle and brown in color. This can be avoided only by taking great care in the halogenation process and even then there is no assurance of obtaining a uniform, sustained, slip film. Waxes and silicone have been used but these provide only a temporary solution as these materials rub off in a very short time. It has further been proposed in U.S. Pat. No. 3,286,011 issued Mar. 18, 1964, and U.S. Pat. No. 3,411,982 issued November 1968, to provide a slip finish comprising a rubber latex and a resin latex. While such coatings reduce the coefficient of friction of the rubber article to a slight extent, it is desirable to further reduce the coefficient of friction. For example, it is desirable to further reduce the coefficient of friction to make it easier to put on and take off a rubber article such as a rubber glove.

In the preparation of rubber articles by dipping into a coagulant solution and then into a rubber latex followed by coagulation of the rubber latex into the desired article, it is usually necessary to first apply to the form a coating of a release agent such as a mold release powder, e.g., talc, diatomaceous earth, etc. or a lubricant type release agent, e.g., glycerine. The reasons for the use of the release agents are (1) to prevent damage to the rubber article when it is stripped from the form and/or (2) to preclude the tendency of the tacky rubber to self adhesion when the article is removed. Use of release agents in the preparation of dipped rubber articles, however, is not without its shortcomings for it naturally leads to adulterated final products which have trapped or otherwise picked up the release agent on the coagulated rubber surface. Nevertheless, the contaminated rubber article is a matter which manufacturers of such articles have had to live with for it has not been possible to obtain these rubber articles in a commercially acceptable form without the use of the release agents.

Another drawback commonly associated with the use of release agents in the manufacture of rubber articles is that the process requires clean up of the residue of the release agent on the mold or form after formation of each and every article, a tedious and time consuming operation.

The same problems necessitating the use of release agents in the formation of rubber article's directly on dipping forms, likewise necessitate the use of release agents in processes such as described in U.S. Pat. No. 3,411,981 to Kavalir, et al. wherein the slip-coated rubber articles are prepared by first providing a release composition onto the form before it is dipped into the rubber latex. In addition to the aforementioned stripping and self-adhesion difficulties, there is a tendency for the slip coating to separate from the rubber substrate when release agents are not utilized in such processes.

Furthermore, in the prior art processes for obtaining slip coatings there has been a tendency for the surface of the articles produced to exhibit streaks.

The foregoing problems were overcome or alleviated by use of the two component synthetic polymer systems described in U.S. Pat. Nos. 4,027,060 and 4,082,862. While rubber articles such as gloves produced using the dual polymer component systems and processes of these patents were excellent, they were not without shortcomings. For one, the entire process takes approximately three hours, a process time considered too long by many. Secondly, the removal of the finished gloves from the forms had to be accomplished by stripping under warm water, an inconvenience that further required yet another final drying step. Thirdly, in the prior art processes, coating of the rubber surface with the polymer systems could not be accomplished when the rubber was cured or partially cured. The coating had to be conducted while the rubber was still hydrated. Lastly, it was difficult, if not impossible, to don the finished glove when the hands are wet or damp.

Thus, it is an object of the invention to provide rubber articles containing slip coatings comprised of non-elastomeric materials which when applied to the rubber substrate take on the elastomeric properties of the substrate.

It is also an object of the invention to provide a process for the production of rubber articles which process does not require the use of release agents as a separate and distinct entity and which nevertheless results in a rubber article having a slip coating which has an appreciably lower coefficient of friction than the rubber surface to which it has been applied.

Yet another objective of the invention is to provide a process for the production of rubber articles substantially reduced in process time where such process time is commensurate with or faster than existing commercial cycles.

Another object of the present invention is to provide a process that enables removal of the finished glove from the forms without having to immerse them in warm water.

Still another object of the invention is to provide a process for the manufacture of rubber articles such as gloves which permits coating over cured, partially cured, or uncured (hydrated) rubber and wherein a second deionized leach step is unnecessary.

Yet another object of the invention is to provide rubber or vinyl articles such as gloves which can be donned with wet or damp hands.

BRIEF SUMMARY OF THE INVENTION

The foregoing and other objects of the invention will be apparent to those having ordinary skill in the art and are achieved according to the present invention by providing a formed article comprising outer and inner rubber or vinyl resin surfaces, at least one of said outer and inner rubber or vinyl surfaces having a first essentially rubber-free extensible adherent slip coating comprising a film-forming copolymer resin Component A comprising the reaction product of about 55 to 80 mole %, preferably about 60 to 70 mole % of at least one copolymerizable vinyl halide, about 15 to 32 mole %, preferably about 20 to 27 mole %, of at least one copolymerizable ethylenically unsaturated hydrocarbon and about 3 to 10 mole %, preferably about 4 to 8 mole % of at least one copolymerizable monomer containing a carboxyl or amido group or a second essentially rubber-free extensible adherent slip coating comprising a film forming copolymer resin Component B comprising the reaction product of about 76 to 94 mole %, preferably 80 to 90 mole % of a copolymerizable vinyl or vinylidene halide, about 4 to 12 mole %, preferably about 8 to 11 mole % of acrylonitrile and about 2 to 12 mole %, preferably about 2 to 6 mole % of at least one acrylic monomer, or mixtures of Component A and Component B.

In a preferred embodiment, the invention provides a formed article comprising outer and inner rubber or vinyl resin surfaces, said outer rubber or vinyl surface having a first essentially rubber-free extensible adherent slip coating comprising a film-forming copolymer resin Component A comprising the reaction product of about 55 to 80 mole %, preferably about 60 to 70 mole % of at least one copolymerizable vinyl halide, about 15 to 32 mole %, preferably about 20 to 27 mole %, of at least one copolymerizable ethylenically unsaturated hydrocarbon and about 3 to 10 mole %, preferably about 4 to 8 mole % of at least one copolymerizable monomer containing a carboxyl or amido group, and said inner rubber or vinyl surface having a second essentially rubber-free extensible adherent slip coating selected from the group consisting of Component A, a film forming copolymer resin Component B comprising the reaction product of about 76 to 94 mole %, preferably 80 to 90 mole % of a copolymerizable vinyl or vinylidene halide, about 4 to 12 mole %, preferably about 8 to 11 mole % of acrylonitrile and about 2 to 12 mole %, preferably about 2 to 6 mole % of at least one acrylic monomer, or mixtures of Component A and Component B.

In another preferred embodiment of the present invention the first slip coating, i.e., the coating on the outer surface, includes a detackifying material. A particularly preferred detackifying material comprises the copolymer resin Component B identified above.

In the preferred embodiment of the present invention, Component B is used on the inner surface; however, with certain rubber substrates, it may be necessary to use either Component A alone or a mixture of Component B and Component A to obtain satisfactory adhesion of the coating to the inner surface of the rubber or vinyl. In such cases a mixture of Component A and Component B is preferred.

In yet another embodiment of the present invention, the second slip coating provided on the inner surface of the article includes a small amount of an alkali metal, alkaline earth metal, ammonium or trialkanolamine salt of a fatty acid of about 8 to 24 carbon atoms. It has been found that this material permits coating over a dry or partially cured rubber or fused vinyl during the manufacturing process.

Further, by adjusting the pH of the base resin emulsion system (i.e. either Component A or Component B or mixtures thereof) anionic, cationic or nonionic surfactants can be used to effect coating over cured, partially cured or uncured (hydrated) rubber.

Aside from the salts of fatty acids described above, other anionic surfactants found effective include the sulfates and sulfonates of oils and fatty acids—for example, sodium dodecylsulfate, sulfated glycerol trioleate, sodium alkylaryl sulfonate, dodecylbenzene sulfonic acid. The esters of sodium sulfosuccinic acid are also useful.

In the nonionic class, octylphenoxypolyethoxyethanol is found to be most effective. Cationics such as tallow triammonium chloride and dicocodimethylammonium chloride have been utilized.

Another preferred embodiment of the invention includes in combination with copolymer resin Component B, a small amount of a poly(alkylene oxide) glycol. It has been found that the presence of this material in combination with the second copolymer resin component provides a dry lubricating coating that offers better wet-hand donnability than when copolymer resin Component B alone is employed.

The use of a polyglycol and a fatty acid salt produces a gel which functions to lubricate the coating and impart a velvety feel to the skin. Gels of varying consistency are produced by the other surfactants depending on functionality.

In another aspect of the invention, there is provided an emulsion of copolymer B containing small amounts of a poly(alkylene oxide) glycol and optionally containing a small amount of a silicone fluid. The silicone can be polydimethylsiloxane or an aminopolysiloxane. Adding silicone in an amount of about 2 to 15% by weight of total solids further improves damp hand donnability while maintaining gel properties. The result is an aesthetically pleasing dry lubricating coating with damp hand donnability in contrast to fluid coatings which produce greasy or oily films on the inside of the glove.

The novel process of the invention comprises coating a form with an aqueous dispersion of copolymer resin Component A or Component B as defined above, or mixtures thereof, preferably a coating comprising Component A to form a first, rubber-free extensible adherent slip coating, forming over said slip coating a rubber or vinyl substrate, at least partially curing the rubber or fusing the vinyl. In a preferred embodiment, the thus formed substrate is then coated with an aqueous dispersion of the copolymer resin Component A or Component B defined above, or a combination of Component A and Component B, and the composite thus formed is dried and stripped off of the form to provide rubber or vinyl articles with improved slip coatings on both the outer and inner surfaces of the article. In the case of surgeons' gloves, when the outer surface is coated with a coating comprising Component A there is thereby produced a glove which can be easily stripped off of the form without submersion in warm water, which is free of any release agent contamination, which can be slipped on and off even when the hands are wet or damp.

In another aspect of the invention there is provided an aqueous dispersion of copolymer resin Component A defined above and detackifying amounts of copolymer resin Component B, optionally containing small amounts of a silicone.

In yet another aspect of the invention there is provided an aqueous dispersion of copolymer resin Component B containing small amounts of an alkali metal, alkaline earth metal, ammonium or trialkanolamine salt of a fatty acid of about 8 to 24 carbon atoms, optionally containing a small amount of poly(alkylene oxide) glycol, and a small amount of polydimethylsiloxane or an amino-polysiloxane.

DETAILED DESCRIPTION OF THE INVENTION

Rubber or Vinyl Surface

The rubber surface on which the slip coating is provided may be fabricated from any suitable conventional latex dipping compound such as those disclosed in U.S. Pat. No. 3,411,982. The latex may be pre-cured or non pre-cured latex in which case the rubber article is cured after forming. The latex dip may contain conventional compounding ingredients commonly utilized. Specific examples are given in U.S Pat. No. 3,411,982. The rubber may be natural rubber or any conventional latex suitable for dipping operations. Of the various natural and synthetic latices, natural rubber, polychloroprene rubber, synthetic polyisoprene, SBR (styrene-butadiene rubber) and mixtures thereof are preferred.

Vinyl surfaces may be prepared from vinyl resins such as polyvinylchloride resin using conventional processes well known in the art.

Conventional formulations for these rubber and vinyl resins are well known in the art and those skilled in the art are readily able to vary the formulations and conditions of curing or fusing and the like to suit the particular latex being used as well as the particular final article desired. Similarly, the articles can vary widely and include gloves, particularly surgeons' gloves, girdles, and the like.

First or Outer Slip Coating

Copolymer resin Component A preferably employed in providing the first slip coating on the outer surface is comprised of the reaction product of at least one copolymerizable vinyl halide, at least one copolymerizable ethylenically unsaturated hydrocarbon and at least one copolymerizable monomer containing a carboxyl or an amido group, in the proportions defined above.

Illustrative of vinyl halides that may be employed are vinyl chloride, vinyl fluoride and vinyl bromide. The preferred vinyl halide is vinyl chloride.

The ethylenically unsaturated hydrocarbon monomers of the copolymer resin Component A are preferably straight and branch-chained alpha-olefins of 2 to 5 carbon atoms such as ethylene, propylene, 1-butene, isobutene, 1-pentene and the like.

The copolymerizable ethylenically unsaturated monomers containing at least one carboxyl or amido group of the copolymer resin Component A are preferably acrylic monomers having the structure:

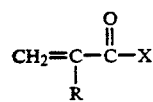

wherein
X is —OH, NH$_2$,

OCH$_3$, OC$_2$H$_5$, OCH$_2$CH$_2$CH$_2$CH$_3$, etc.
R is an H or methyl.

Examples of suitable acrylic monomers are acrylic acid, methacrylic acid, and esters of acrylic acid and methacrylic acid preferably up to 12 carbon atoms such as methyl acrylate, ethyl acrylate, n-butyl acrylate, isobutyl acrylate, 2-ethylhexyl acrylate, lauryl acrylate, and similarly methyl methacrylate, ethyl methacrylate, n-butyl methacrylate, isobutyl methacrylate, 2-ethylhexyl methacrylate, lauryl methacrylate, acrylamide, methacrylamide, N-methylolacrylamide, etc; and mixtures thereof.

The preferred ethylenically unsaturated hydrocarbon monomer is a mixture of acrylamide and acrylic acid in a ratio, preferably between 1:1 and 3:1.

It has been found that copolymer resin Component A is essential for proper release of the substrate from the form and permits release from a bisque form without the necessity of carrying out the removal while submerged under warm water. Until copolymer resin Component A was used in the outer slip coating it was impossible to strip from a bisque form. Heretofore, prior art systems required glazed porcelain forms to produce a powderless glove with the very smooth surface of the glazed porcelain form facilitating removal from the form. However, even with the glazed forms, removal had to be effected under water. The ease of release from bisque forms is surprising since the polar groups present in copolymer resin Component A are expected to interfere with good release.

Thus, where Component B is used alone as the outer slip coating it will be necessary to effect removal from porcelain forms while submerged under water pursuant to prior art techniques as described, for example, in U.S. Pat. Nos. 4,027,060 and 4,082,862, hereby incorporated by reference.

When employed the detackifier component of the first slip coating is present in detackifying amounts generally falling in the range of about 10 to 25% by weight of the total solids.

The detackifier component preferably used in combination with the first resin component can be any of the detackifier resins conventionally used for this purpose such as waxy materials, for example, cetyl alcohol, stearic acid esters, polyethylene emulsions and the like. Preferred, however, is a copolymer resin Component B comprising the reaction product of vinylidene or vinyl halide, acrylonitrile and an acrylic monomer. By "acrylic monomer" as used in this specification and the appended claims, is meant a copolymerizable acrylic acid, lower alkyl acrylic acid and the esters of acrylic acid and lower alkyl acrylic acid.

The silicone component, optionally included in the first or outside slip coating, can be any of the well known polysiloxanes commonly referred to as silicones and preferably comprised of organopolysiloxane, a dialkylsiloxane polymer, or an aminopolysiloxane. Especially preferred is dimethylsiloxane polymer. It has been found that the presence of small amounts of the polysiloxane induces suppleness to the finished rubber article. When used, therefore, it is added in an amount that increases the suppleness of the outer slip coating. In general, these amounts fall in the range of about 0.001 to 0.5% by weight of the total solids. If preferred, this silicone component can be formulated into the rubber latex also to further add suppleness to the end product.

Second or Vinyl Inner Slip Coating

If a second or inner slip coating is applied it can be either Component A described above but is preferably Component B. The copolymer resin Component B of the second slip coating comprises the reaction product of a copolymerizable vinyl or vinylidene halide, acrylonitrile and acrylic monomer in the portions defined above. As aforementioned, copolymer resin Component B of the second slip coating has been found to provide an inner coating on rubber or vinyl gloves that facilitates the donning of the gloves when the hands are wet or damp. Preferred amongst this class of copolymer resins is the copolymer vinylidene halide, acrylonitrile and methylmethacrylate.

It is preferred to include as part of the inner slip coating an alkali metal, alkaline earth metal, ammonium or trialkanolamine salt of a fatty acid having about 8 to 24 carbon atoms. The preferred fatty acid salts are the alkali metal or triethanolamine salts of fatty acids of 12 to 20 carbon atoms. Especially preferred is cesium stearate, cesium myristate, cesium palmitate and triethanolamine stearate, myristate or palmitate. The presence in the slip coating of preferably 5 to 15% by weight (solids basis) of these fatty acid salts has been found to permit coating over dried or partially cured rubber. This eliminates the most critical part of the prior art processes which require thorough washing of the coagulated rubber in deionized water after a standard leach to remove any residual divalent ions such as $Ca^{++}$ and then polymer coating the rubber surface while the rubber was relatively dry but still hydrated. In the prior art processes if the rubber was too wet or too dry (partially-cured) polymer pick-up and therefore coating was impossible. Thus, the fatty acid salt component of the invention permits coating over dry or partially-cured rubber. As mentioned previously, by adjusting the pH of the emulsified resin Component B (or mixtures of resin component A & B) either anionic, cationic or nonionic surfactants can be used to effect coating over cured or uncured rubber.

Even better wet-hand donnability is obtainable if there is included in the second slip coating a polyhydroxyfunctional polymer comprising poly(alkylene oxide) polyol. Not all the alkylene units need be the same. Poly(alkylene oxide) polyols formed by the copolymerization or condensation of mixtures of different cyclic ethers, glycols, or glycols and cyclic ethers can be used; as can poly(alkylene oxide) polyols derived from cyclic ethers such as dioxolane, which affords a polyol having the formula $HO(CH_2-OCH_2CH_2O)_nH$, where n is greater than 1. The alkylene segment can be a straight or a branched chain, as in poly(propylene oxide) polyol. In the case where the alkylene unit is ethylene, it can be advantageously to incorporate the unit into a copolymer, for example, as a copolymer of ethylene oxide and propylene oxide, with up to 80 percent of such copolymer comprising ethylene oxide. Representative poly(alkylene oxide) polyols include poly(ethylene oxide) polyols, poly(propylene oxide) polyols, poly(tetramethylene oxide) polyols, poly(nonamethylene oxide) polyols, poly(oxymethylene-ethylene oxide) polyols, poly(ethylene oxide-propylene oxide) polyols, and poly(pentaerythritolethylene oxide) polyols. Thus, the poly(alkylene oxide) polyols will generally have from 2 to 6 hydroxyl groups with such polyols having 2 hydroxyl groups being currently preferred. Preferred poly(alkylene oxide) polyols are poly(ethylene oxide) polyols, poly(propylene oxide) polyols, and poly(ethylene oxide-propylene oxide) polyols.

Also functional in this application are polypropylene glycol esters, polyethyleneglycol esters and polyglycerol esters. Polyethyleneimine resins have also been used successfully.

When utilized, the poly(alkylene oxide) polyol is employed in amounts ranging from about 5 to 50% by weight (solids basis), preferably about 5 to 30%. Excessive concentrations of poly(alklene oxide) tend to induce an undesirable oiliness to the finished product.

Thus, while use of the second copolymer resin by itself improves wet-hand donnability, even better results are achieved when poly(alkylene oxide) polyol is employed in combination with the resin. Of interest is the fact that even when liquid poly(alkylene oxide) polyols are used in combination with the second copolymer resin, surprisingly the end product is a dry coating of uniform lubrication even though a film of pure second copolymer resin and the polyglycol used are incompatible. Although the reason for this phenomena is not known for certain, one explanation is that the use of a polyglycol and a fatty acid salt produces a gel which is trapped within the copolymer resin Component B as the film coalesces producing a dry appearance. The polyglycol/fatty acid salt gel is released in minuscule amounts as the glove is stressed, for example, during donning—thereby providing the lubricating function and yet always appearing dry and aesthetically pleasing. Another explanation is an ester interchange reaction with the methylmethacrylate group of the second copolymer resin which results in a chemical linkage between the resin and the glycol. Adding about 2-15% by weight of total solids of silicone further improves damp hand donnability while maintaining gel properties. That gel properties are maintained is postulated on the basis of silicone fluid reaction through the OH function producing pendant silicone groups on the glycol. Further, amino functional silicones can react with the acid or ester component of the second resin system thereby attaching to the base resin by primary bonding forming a branched polymer/polymer alloy in situ.

The above reactions would occur during the precure cycle as the water of dispersion is evaporating and the polymer film is coalescing The result is a cosmetically-appealing, dry lubricating coating.

The improved slip coatings according to the invention are preferably provided on a rubber or vinyl surface by contacting the surface with an aqueous dispersion consisting essentially of water and the copolymer resins. Alternatively, the slip coating can be first provided on a form and the form subsequently dipped into a rubber latex as disclosed in U.S. Pat. No. 3,411,982.

The slip coating provided by the present invention has excellent characteristics of slipperiness. A simple way to demonstrate the slipperiness of substrates coated according to the invention is to place two coated surfaces together and rub the surfaces back and forth while grasped between the fingers. Previous slip coatings which have been tested slip poorly when held in this manner. However, the coatings provided by the present invention show a marked slip. Furthermore, the coatings provided by the present invention are tenaciously adhesive and the rubber substrate can be stretched to maximum extent without affecting the slipperiness of and without causing cracking of the slip coating according to the present invention.

According to a preferred embodiment of the present invention a form for the desired article is preferably heated and provided as by dipping with an aqueous dispersion consisting essentially of water and the copolymer resin Component A. The resin coating is dried on the form and provided with a coagulant such as a solution of calcium nitrate and isopropanol after which it is dipped into a tank containing rubber latex solution. The rubber latex solution generally varies from 25 to 50% solids depending upon the thickness and the viscosity of the desired product. The immersion time into the tank will vary depending on the desired thickness and in general the dip time will extend from about 3 seconds to 1 minute. After the formation of the rubber substrate the coagulant therein is leached, for instance, by dipping the resulting form into a leach tank containing hot water which is usually at a temperature ranging from about 135° to 140° F.

The article is then partially cured by heating at approximately 200° F. for 15 minutes. In this instance there results a product the outer surface of which contains the first resin slip coating. The second slip coating of the invention is then applied to the partially cured rubber substrate as an aqueous dispersion consisting essentially of water and copolymer resin Component B. The second resin slip coating is then dried and the resin-rubber-resin composite is stripped off the form.

The following examples are included to further illustrate the process of the present invention.

EXAMPLE 1

A bisque glove form is cleaned by pointing it down in a tank of M-Pyrol and soaking for five minutes at room temperature. The form is then later rinsed and dried. The dried form is then dipped into a first polymer coating system of 5% solids and 95% water. Of the 5% solids, 85% is comprised of a) an emulsion at 49% solids of:

| | | |
|---|---|---|
| Vinylchloride | 69% | |
| Ethylene | 25% | |
| Acrylamide | 4% | |
| Acrylic Acid | 2% | |

15% of b) an aqueous dispersion at 54% solids of:

| | | |
|---|---|---|
| Vinylidene chloride | 85% | |
| Acrylonitrile | 10% | |
| Methylmethacrylate | 4.5% | | and 0.025% silicone emulsion (a non-ionic emulsion containing 35% dimethylpolysiloxane).

The dip coated form is baked in an oven with the form pointing up at 225° F. for 2 to 3 minutes. The coated glove form is dipped with the form pointing down into a rubber coagulant (calcium nitrate) maintained at 110° F. and then into an aqueous natural rubber latex (35% solids) for 20 to 30 seconds. At the point when the form is completely out of rubber latex, and no further dripping takes place, the form is rotated so that the fingertips are in the up position to distribute the last drop of rubber and subjected to a conventional leaching step at approximately 150° F. for 15 minutes followed by oven curing at approximately 200° F. for 15 minutes. The form containing the first polymer system rubber composite coating is then dipped into a second polymer system composed of 6% solids and 94% water. 5% of the solids is aqueous dispersion (b) to which is added 0.5% by weight cesium stearate and 0.5% by weight polypropylene glycol. The thus coated glove is dried with the fingers up at 205° F. for 1 minute and then stripped from the mold. Note: the mold is now ready for further glove making without the necessity of cleaning—simply dip into resin Component A and start the cycle all over again.

EXAMPLE 2

Example 1 above is repeated except after the leach the rubber is precured for approximately 5 minutes at 200° F. The form containing the first polymer system rubber composite is now dipped into the second polymer system described above and then cured in an oven for the remaining 10 minutes at 200° F.

EXAMPLE 3

Example 1 above is repeated except along with the cesium stearate and polypropylene glycol gel a silicone is added in an amount of approximately 10% by weight of total solids. The silicone can be polydimethylsiloxane or amino-polysiloxane. This amount of silicone incorporated does not interfere with the lubricating gel produced by the cesium stearate and polyglycol. Further, the amine function of the polysiloxane can react with the acid or ester component of the second resin system thereby attaching itself to the base resin by primary bonding forming a polymer alloy.

EXAMPLE 4

A bisque glove form is cleaned by pointing it down in a tank of M-Pyrol and soaking for five minutes at room temperature. The form is then rinsed and dried. The dried form is then dipped into a first polymer coating system of 6% solids and 94% water. The 6% solids is resin Component A which consists of an emulsion of the following:

| | | |
|---|---|---|
| Vinylchloride | 69% | |
| Ethylene | 25% | |
| Acrylamide | 4% | |
| Acrylic Acid | 2% | |

Additionally, 0.01 to 0.3% by weight of polypropyene glycol or 0.025% by weight of a silicon emulsion or both can be added as detackifiers. The dip coated form is heated in an oven with the form pointing up at 225° F. for 2 to 3 minutes. The coated glove is dipped with the form pointing down into a rubber coagulant maintained at 110° F. and then into an aqueous natural rubber latex (35% solids) for 20 to 30 seconds. At the point when the form is completely out of rubber latex, and no further dripping takes place, the form is rotated so that the fingertips are in the up position to distribute the last drop of rubber and subjected to a conventional leaching step at approximately 150° F. for 15 minutes followed by oven drying of the surface water (approximately 30 seconds). The form containing the first polymer system rubber composite coating is then dipped into a second tank of Component A resin system at 6% solids and 94% water. In this second dip tank, of the 6% solids, 4.5% is resin Component A described above to which is added 0.75% solids by weight of cesium stearate and 0.75% solids by weight of polypropylene glycol. The thus coated glove is cured with the fingers up at 200° F. for 10–15 minutes, cooled and stripped from the mold. The mold is now ready for further glove making without the necessity of cleaning—simply dip into resin Component A and start the cycle all over again.

EXAMPLE 5

Example 4 is repeated except that along with the cesium stearate and polypropylene glycol gel, a silicone is added in an amount of approximately 10% by weight of total solids. The silicone can be the same as that employed in Example 3 above.

EXAMPLE 6

A bisque glove form is cleaned by pointing it down in a tank of M-Pyrol and soaking for five minutes at room temperature. The form is then rinsed and dried. The dried form is then dipped into polymer coating system B at 6% solids and 94% water. The 6% solids is resin Component B which consists of an aqueous dispersion of the following:

| | | |
|---|---|---|
| Vinylidene chloride | 85.0% | |
| Acrylonitrile | 10.0% | |
| Methylmethacrylate | 4.5% | |

Additionally, 0.01 to 0.3% by weight of polypropylene glycol or 0.025% by weight of silicone emulsion can be added.

The dip coated form is heated in an oven with the form pointing up at 225° F. for 2 to 3 minutes. The coated glove is dipped with the form pointing down into a rubber coagulant maintained at 110° F. and then into an aqueous natural rubber latex (35% solids) for 20 to 30 seconds. At the point when the form is completely out of the rubber latex, and no further dripping takes place, the form is rotated so that the fingertips are in the up position to distribute the last drop of rubber and subjected to a conventional leaching step at approximately 150° F. for 15 minutes followed by oven drying of the surface water (approximately 30 seconds). The form containing polymer coating system B rubber composite is then dipped into a second tank of polymer coating system B at 6% solids and 94% water. In this second dip tank, of the 6% solids, 4.5% is resin Component B described above to which is added 0.75% solids by weight of cesium stearate and 0.75% by weight of polypropylene glycol. The then coated glove is cured with the fingers up at 200° F. for 10–15 minutes. Note: in this case with resin component system B on both sides, the glove will have to be stripped hydrated, e.g., submerged in a warm water bath for 10 minutes, removed from the bath and subsequently stripped and dried. The mold, however, is ready for further glove making without the necessity of cleaning—simply dip into resin Component system B and start all over again.

EXAMPLE 7

Example 6 is repeated except that along with the cesium stearate and polypropylene glycol gel a silicone is added in an amount of approximately 10% by weight of total solids. The silicone can be the same as employed in Example 3 above.

It is claimed:

1. A formed article comprised of outer and inner rubber or vinyl resin surfaces, at least one of said outer and inner surfaces having an essentially rubber-free extensible adherent slip coating selected from the group consisting of (i) a first film-forming copolymer resin Component A comprising the reaction product of about 55 to 80 moles % of at least one copolymerizable vinyl halide, about 15 to 32 mole % of at least one copolymerizable ethylenically unsaturated hydrocarbon and about 3 to 10 mole % of at least one copolymerizable ethylenically unsaturated monomer containing a carboxyl or amido group; (ii) a film-forming copolymer resin Component B comprising the reaction product of 76 to 94 mole % of at least one copolymerizable vinyl or vinylidene halide, about 4 to 12 mole % of acrylonitrile and about 2 to 12 mole % of at least one acrylic monomer; and (iii) a film forming mixture of Component A and Component B.

2. A formed article according to claim 1 wherein the surfaces are rubber surfaces and the copolymer resin Component A comprises a film-forming copolymer of vinyl halide, alpha-olefin of up to 4 carbon atoms and acrylamide and acrylic acid.

3. A formed article according to claim 2 wherein the vinyl halide is vinyl chloride.

4. A formed article according to claim 2 wherein the alpha-olefin is ethylene.

5. A formed article comprised of outer and inner rubber or vinyl resin surfaces, said outer rubber or vinyl surface having a first essentially rubber-free extensible adherent slip coating comprising a first film-forming copolymer resin Component A comprising the reaction product of about 55 to 80 moles % of at least one copolymerizable vinyl halide, about 15 to 32 mole % of at least one copolymerizable ethylenically unsaturated monomer containing a carboxyl or amido group and said inner rubber or vinyl surface having a second essentially rubber-free extensible adherent slip coating selected from the group consisting of Component A, a film-forming copolymer resin Component B comprising the reaction product of 76 to 94 mole % of at least one copolymerizable vinyl or vinylidene halide, about 4 to 12 mole % of acrylonitrile and about 2 to 12 mole % of at least one acrylic monomer, and mixtures of Component A and Component B.

6. A formed article according to claim 5 wherein the first slip coating includes an effective amount of a detackifying material.

7. A formed article according to claim 6 wherein the detackifying material is copolymer resin Component B of claim 1.

8. A formed article according to claim 7 wherein the detackifying material is a copolymer of about 80 to 90 mole % of vinylidene chloride, about 8 to 11 mole % of acrylonitrile, and about 2 to 6 mole % of methylmethacrylate.

9. A formed article according to claim 7 wherein the detackifying copolymer is added in an amount of about 10 to 25 % by weight.

10. A formed article according to claim 6 wherein the detackifying material is a poly(alkylene oxide) polyol.

11. A formed article according to claim 10 wherein the poly(alkylene oxide) glycol is polypropylene glycol.

12. A formed article according to claim 5 wherein the first slip coating contains polysiloxane in an amount sufficient to increase the suppleness of the slip coating.

13. A formed article according to claim 12 wherein the amount of polysiloxane is about 0.001 to 0.5 % by weight.

14. A formed article according to claim 5 wherein copolymer resin Component B comprises the film-forming reaction product of about 80 to 90 mole % of vinyl halide or vinylidene halide, about 8 to 11 mole % of acrylonitrile and about 2 to 6 mole % of acrylic monomer.

15. A formed article according to claim 14 wherein the copolymer resin Component B comprises the reaction product of vinylidene chloride, acrylonitrile and methylmethacrylate.

16. A formed article according to claim 5 wherein the second slip coating includes alkali metal, alkaline earth metal, ammonium or trialkanolamine salt of a fatty acid having 8 to 24 carbon atoms in an amount of about 2 to 25% by weight.

17. A formed article according to claim 16 wherein the salt of the fatty acid is an alkali metal fatty acid salt.

18. A formed article according to claim 17 wherein the alkali metal fatty acid salt is cesium stearate.

19. A formed article according to claim 16 wherein the second slip coating includes a poly(alkylene oxide) polyol in an amount of about 5 to 50% by weight.

20. A formed article according to claim 19 wherein the amount of poly(alkylene oxide) polyol is about 15 to 30% by weight.

21. A formed article according to claim 20 wherein the poly(alkylene oxide) polyol is polyethylene glycol.

22. A formed article according to claim 20 wherein the poly(alkylene oxide) is polypropylene glycol.

23. A formed article according to claim 22 wherein the polypropylene glycol is non-water-soluble polypropylene glycol having a molecular weight about 500 and said polypropylene glycol is emulsified using cesium stearate, potassium stearate or other alkali metal fatty acid.

24. A formed article according to claim 5 wherein the rubber or vinyl substrate includes a polysiloxane emulsion in an amount sufficient to improve suppleness of the article formed.

25. A formed article according to claim 5 wherein Component A or B as the inner or second slip coating includes about 2 to 25% by weight of an alkali metal, alkaline earth metal, ammonium or trialkanolamine salt of a fatty acid of about 8 to 24 carbon atoms.

26. A formed article according to claim 5 wherein Component A or B further includes about 5 to 50% by weight of poly(alkylene oxide) polyol or polyalkyleneglycol ester.

27. A formed article according to claim 26 wherein Component A or B includes up to 10% of an emulsified polydimethylsiloxane or aminopolysiloxane.

* * * * *